United States Patent
McNamee

(10) Patent No.: US 6,186,956 B1
(45) Date of Patent: Feb. 13, 2001

(54) METHOD AND SYSTEM FOR CONTINUOUSLY MONITORING CARDIAC OUTPUT

(75) Inventor: James E McNamee, Columbia, SC (US)

(73) Assignee: University of South Carolina, Columbia, SC (US)

( * ) Notice: Under 35 U.S.C. 154(b), the term of this patent shall be extended for 0 days.

(21) Appl. No.: 09/318,594

(22) Filed: May 25, 1999

Related U.S. Application Data

(60) Provisional application No. 60/086,968, filed on May 28, 1998.

(51) Int. Cl.$^7$ ........................................................ A61B 5/00
(52) U.S. Cl. .......................... 600/526; 600/529; 600/534; 600/538
(58) Field of Search ................................. 600/529, 534, 600/538, 526, 504, 505

(56) References Cited

U.S. PATENT DOCUMENTS

| | | | |
|---|---|---|---|
| 4,083,367 | * | 4/1978 | Portner et al. ........................ 600/538 |
| 4,608,995 | * | 9/1986 | Linnarsson et al. ................. 600/538 |
| 4,949,724 | * | 8/1990 | Mahutte et al. ..................... 600/526 |
| 4,966,141 | * | 10/1990 | Bacaner et al. ..................... 600/532 |
| 5,178,151 | * | 1/1993 | Sackner ................................ 600/526 |
| 5,287,851 | * | 2/1994 | Beran et al. ......................... 600/538 |
| 5,836,300 | * | 11/1998 | Mault .................................... 600/532 |
| 5,971,934 | * | 10/1999 | Scherer et al. ...................... 600/532 |
| 6,042,550 | * | 3/2000 | Haryadi et al. ...................... 600/504 |

* cited by examiner

Primary Examiner—Robert L. Nasser
(74) Attorney, Agent, or Firm—Michael E. Wever; Michael A. Mann; Nexsen Pruet Jacobs and Pollard

(57) ABSTRACT

The present invention is a method and system for continuously monitoring cardiac output. In a preferred embodiment, the method and system of the present invention comprises a pneumotachograph, differential pressure transducer, and a signal amplifier/conditioner interconnected to a programmed digital computer. A patient, preferably, inserts the pneumotachograph in his mouth or, alternatively, the pneumotachograph is connected to a patient's tracheal cannula. As the patient exhales and inhales the differential pressure transducer measures the drop in pressure as air flows through the pneumotachograph thereby producing a weak electrical signal non-linearly proportional to flow. Next, the weak signal is directed through the amplifier/signal conditioner which increases the amplitude and removes some of the noise contained in the transducer output. A digital computer is then utilized to convert the analog time varying electrical signal into a stream of digital data, store it on disk, display it in real time and processes the signal using an experimentally determined correlation factor and mathematical equations relating the fluctuations in air flow with stroke volume to obtain the cardiac output.

20 Claims, 1 Drawing Sheet

METHOD AND SYSTEM FOR CONTINUOUSLY MONITORING CARDIAC OUTPUT

This application claims the benefit of U.S. Provisional Application No. 60/086,968, filed on May 28, 1998.

BACKGROUND OF THE INVENTION

1. Field of the Invention

The present invention relates to a method and system for monitoring cardiac output. In particular, the present invention relates to a method and system for continuously monitoring cardiac output without injection or withdrawal of liquids into the patient.

2. Discussion of Background

Accurately measuring and monitoring cardiac output has long been a clinical and research goal. Both direct and indirect methods are known. Because the history of cardiac monitoring goes back to the early part of this century, there have been many techniques devised. A representative rather than an exhaustive list has been prepared to summarize the methods employed.

One technique known as the "direct method" is the most accurate but is largely restricted to the research laboratory because of the massively invasive or traumatic procedures which must be employed. Less destructive, indirect methods include steady-state Fick oxygen uptake, the transient indicator dilution method, and anemometry.

Of these invasive methods, the transient indicator dilution procedure using iced liquids injected through the lumen of a Swan-Ganz catheter is currently the most frequently employed clinical method. It requires the least amount of specialized equipment, is portable to the patent's bedside and can be repeated often. However, the transient indicator dilution procedure requires a specially trained physician to thread an expensive catheter through the right side of the heart and into the pulmonary artery. During long term monitoring, infection at the site of catheter insertion and damage to the blood vessels of the lung are constant hazards. Swan-Ganz catheters may also need to be repositioned or replaced after a few days of use. Accuracy and repeatability of the thermal dilution Swan-Ganz method are typically no better than 10% even under precisely controlled laboratory conditions.

Non-invasive indirect methods include the ballistocardiography method which requires a patient to lie motionless on a large inertial platform, the soluble gas uptake method which requires a patient to sit in a small chamber for many minutes and the impedance plethysmography method which measures small changes in electrical impedance on the surface of the chest.

The first two non-invasive methods are not readily utilized because the special equipment needed is extremely large and inconvenient to use. In addition, with impedance plethysmography, accuracy is difficult to obtain and thus, it is a less favored method.

Representative heart imaging techniques include 2-D cineangiography and 2D echo cardiography in which a series of x-ray or ultrasound images of the beating heart are measured to determine left ventricle systolic and diastolic volumes. 3-D ECG-gated MRI and radioactive imaging methods where many images of the heart are made during particular phases of the cardiac cycle can also be employed. These methods require large, expensive equipment, and measurements are time consuming and require the efforts of several highly trained specialists to obtain and interpret results.

Therefore, there is a need for a non-invasive and relatively inexpensive device and method for continuously monitoring a patient's cardiac output that can be easily utilized at the bedside or in a physician's office and does not require injection or withdrawal of fluid from the body.

SUMMARY OF THE INVENTION

According to its major aspects and broadly stated, the present invention is a method and system for continuously monitoring cardiac output. In a preferred embodiment, the method and system of the present invention comprises a pneumotachograph, differential pressure transducer, and a signal amplifier/conditioner interconnected to a programmed digital computer. A patient, preferably, inserts the pneumotachograph in his mouth or, alternatively, the pneumotachograph is connected to a patient's tracheal cannula. As the patient exhales and inhales the differential pressure transducer measures the drop in pressure as air flows through the pneumotachograph thereby producing a weak electrical signal non-linearly proportional to flow. Next, the weak signal is directed through the amplifier/signal conditioner which increases the amplitude and removes some of the noise contained in the transducer output. A digital computer converts the analog time varying electrical signal into a stream of digital data, stores it on disk, displays it in real time and processes the signal using an experimentally determined correlation factor and mathematical equations relating the fluctuations in air flow with stroke volume to obtain the cardiac output.

An ideal setting for employing this device is on a patient connected to a mechanical ventilator. The patient is already intubated so the trachea cannot be closed by the epiglottis. Insertion of the air flow measuring portion of this device into the tubing connected by the tracheal cannula to the ventilator is a simple tubing connection.

A second favorable setting is during general anesthesia for operative procedures not requiring the opening of the chest (thoracotomy). This might include orthopedic, abdominal and plastic surgeries.

The system is inexpensive enough that it could also be utilized to monitor a patient's cardiac output during an exercise stress test in a primary care physician's office.

Another feature of the present invention is the non-invasive method used thus resulting in a less intrusive and costly procedure for accurately and continuously monitoring cardiac output.

In addition, because the system is relatively small and light weight, it may be easily moved to the patient or transported along with the patient (i.e., during an ambulance transfer).

Other features and advantages of the present invention will be apparent to those skilled in the art from a careful reading of the Detailed Description of a Preferred Embodiment presented below and accompanied by the drawings.

DETAILED DESCRIPTION OF A PREFERRED EMBODIMENT

Figure 1:
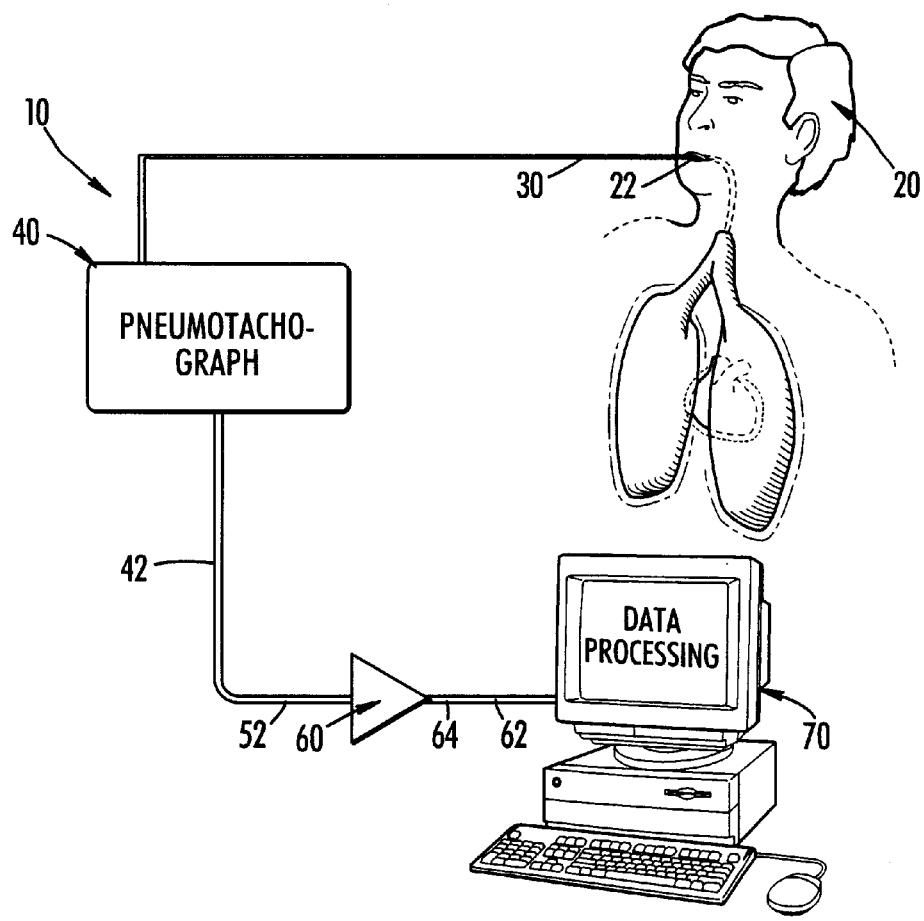
FIG. 1 is a block diagram of the system utilized on a non-intubated patient, according to a preferred embodiment of the present invention.

The present invention is a method and apparatus for measuring heart output, which is the amount of blood pumped by a heart in a given period of time. The measurement, rather than being a direct measurement of blood flow from the heart, is of air flow in the throat based on the theory that the beating heart influences that air flow by pressing on the lungs.

The heart lies inside the airtight chest and is surrounded by the lungs. The heart is filled with blood, an incompressible fluid. When the left side of the heart beats, it ejects a certain quantity of blood which is called stroke volume (SV). Most of the SV leaving the left ventricle of the heart leaves the chest through the aorta. At a heart rate of 77 beats/min, SV in the average healthy adult is approximately 65 ml. The sudden ejection of blood from the closed chest decreases the total volume of the chest cavity.

The chest wall is compliant thus it will expand or contract when the pressure exerted by, or the volume of, its contents change. Because of its compliance (Ccw), the chest wall will become slightly smaller when the heart ejects blood into the aorta. The lung has a compliance (CL) and it, too, will change in size when the heart beats. For a change in the heart volume of SV, the lungs will apportion that volume change between them with the lung changing by SV/(1 +Ccw/CL). Lung and chest wall compliance are nearly equal in the healthy adult. Thus, when the heart beats, the lungs and the chest wall should each change in volume by approximately 0.5*SV.

Neither lung nor chest wall volume can change instantaneously. Airway resistance impedes changes in lung volume while tissue resistance and inertia impede chest wall motions. The compliance of the lung together with airway resistance combine to form a characteristic time constant that limits how rapidly lungs fill or empty. The time constant is approximately 0.1–0.3 seconds in the normal adult chest. This is also about the time required for the heart to eject blood into the aorta (systole). The lung's time constant diminishes the quantity of air that is able to move into the lungs during systole by approximately 30%. From these considerations, lung volume would be expected to increase by about 20–25 ml during ejection in the average resting adult.

In reality, the anatomy and physiology inside the heart are more complex. The heart has four chambers which fill and eject blood at different times during the cardiac cycle. The large blood vessels inside the chest (aorta and vena cavae) are compliant and change volume during the cardiac cycle. The heart moves during filling and ejection and may transmit inertial forces to the diaphragm further changing the chest volume during the cardiac cycle. Each of these factors can potentially complicate this simple explanation of how the pumping heart acts to change lung volume during the cardiac cycle. More work is required to understand the magnitude and significance of these factors on the movement of air into the lungs in response to the beating heart.

Compared to the volume of air typically moved in and out of the lungs with each breath (350–1000 ml), heart induced air flow oscillations, herein referred to as cardiogenic oscillations, are minuscule. In order to detect them it is best to measure during periods of apnea where respiratory air flow is absent. An example of a brief apnea is the interval following several deep breaths. Conventional air flow measuring technology for humans is designed to measure flow rates of 1–10 L/s whereas cardiogenic oscillations are on the order of 0.1 L/s or less. Extra amplification is required to reliably detect these tiny air flow signals. To verify acquisition and facilitate analysis, cardiogenic air flow signals are digitized and recorded on a digital computer.

An obvious requirement for the observation of cardiogenic oscillations in respiratory air flow measured at the mouth is that the trachea must remain open. Experience teaches us that many people close their epiglottis when they are neither inhaling or exhaling, thereby sealing their trachea. It is possible to measure cardiogenic oscillations during breathing in these people by selectively extracting these tiny oscillations from the much larger fluctuations of air flow. Cardiac oscillations are generally of higher frequency than respiratory rhythm and are always physically related to the electrical activity of the normal heart. This knowledge is used to extract only the cardiogenic oscillations in the presence of background respiratory air flow by application of certain time and/or frequency domain methods.

Measured cardiogenic air flow signals are integrated to obtain beat-by-beat volume changes. These values are corrected for lung and chest wall compliance and resistance effects to obtain estimated stroke volume. When these corrected volumes are multiplied by the heart rate, also obtained from cardiogenic oscillations, estimated cardiac output is obtained.

Figure 2:
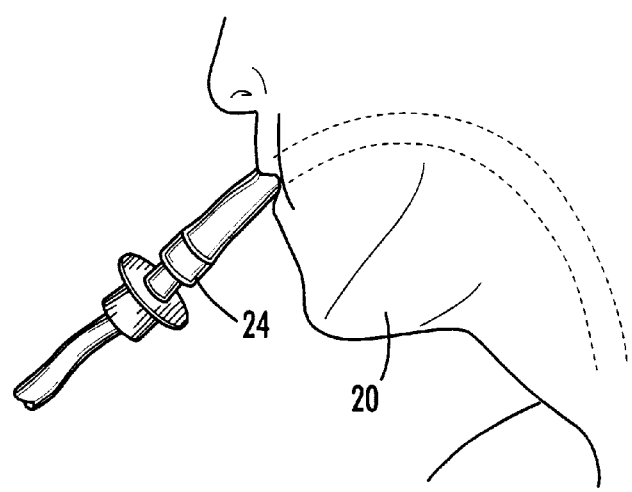
FIG. 2 is a block diagram of the system utilized on a intubated patient, according to a preferred embodiment of the present invention.

Referring now to FIG. 1 and FIG. 2, the block diagram represents a preferred embodiment of system 10. Preferably, inlet tube 30 of pneumotachograph 40 is inserted into patient's 20 mouth 22, or alternatively, if patient is intubated, inlet tube 30 of pneumotachograph 40 is connected to patient's tracheal cannula 24. As patient 20 breathes, differential pressure transducer 40 measures small drops in pressure and produces a weak electrical signal 42 which is non-linearly proportional to flow. Electrical signal 42 travels through first cable 52 to amplifier/signal conditioner 60. Amplifier/signal conditioner 60 increases the amplitude of electrical signal 42 and removes some of the noise contained in electrical signal 42. The amplified signal output 64 then travels through second cable 62 to digital computer 70. Digital computer 70 by use of a computer program converts the analog time varying amplified electrical signal 64 into a stream of digital data, stores it on disk, displays it in real time and processes the signal using an experimentally determined correlation factor and mathematical equations (see below) relating fluctuations in the air flow with stroke volume to obtain cardiac output information.

Because the compliance of the lungs (CL) will vary proportionally with the quantity of blood, stroke volume (SV), ejected by the heart, small air flow oscillations are induced and detectable from the air flow output of the lungs. As air flows through pneumotachograph 40 these cardiogenic oscillations are of a small order and thus must be amplified by amplifier/signal conditioner 60 to be reliably detected.

For a change in the heart volume of SV, the lungs and chest wall will apportion the volume change between them with the lung changing by SV/(1+Ccw/CL). Lung and chest wall compliance are nearly equal in the healthy adult. Thus, when the heart beats, the lungs and the chest wall should each change in volume by approximately 0.5*SV. Computer 70 utilizing a computer program will use the amplified signal output 64 to continuously calculate and display in real time an easily interpretable cardiac output for patient 20.

It will be apparent to those skilled in the art of blood output measurements that modifications and substitutions can be made to the foregoing preferred embodiment without departing from the spirit and scope of the present invention.

What is claimed is:

1. A system for continuously monitoring cardiac output of a patient, said system comprising:

measuring means for measuring air flowing through the throat of a patent;

generating means in operational connection with said measuring means for generating an electrical output signal proportional to the air flow measured by said measuring means; and processing means in operational connection with said generating means for processing said electrical output signal to extract cardiogenic oscillations, to monitor cardiac output.

2. The system as recited in claim 1, wherein said measuring means is a pneumotachograph having a tube that is capable of insertion into the mouth of a patient.

3. The system as recited in claim 1, wherein said measuring means is a pneumotachograph having a tube that is capable of insertion into the tracheal cannula of a patient.

4. The system as recited in claim 1, wherein said processing means amplifies said electrical output signal in order to extract cardiogenic oscillations.

5. The system as recited in claim 1, further comprising conversion means in operational connection with said processing means for converting said electrical output signal into a stream of digital data.

6. The system as recited in claim 1, further comprising calculation means in operational connection with said processing means for calculating cardiac output based on said extracted cardiogenic oscillations.

7. A system for continuously monitoring cardiac output of a patient, said system comprising:

measuring means for measuring air flowing through the throat of a patent;

generating means in operational connection with said measuring means for generating an electrical output signal proportional to the air flow measured by said measuring means;

amplification means in operational connection with said generating means for amplifying said electrical output signal; and processing means in operational connection with said amplification means for processing said electrical output signal to extract cardiogenic oscillations, to monitor cardiac output.

8. The system as recited in claim 7, wherein said measuring means is a pneumotachograph having a tube that is capable of insertion into the mouth of a patient.

9. The system as recited in claim 7, wherein said measuring means is a pneumotachograph having a tube that is capable of insertion into the tracheal cannula of a patient.

10. The system as recited in claim 7, further comprising conversion means in operational connection with said processing means for converting said electrical output signal into digital data.

11. The system as recited in claim 7, further comprising calculation means in operational connection with said processing means for calculating cardiac output based on said extracted cardiogenic oscillations.

12. A method for continuously monitoring the cardiac output of a patient comprising the steps of:

measuring the air flow in the throat of a patient; and extracting monitoring cardiac output by cardiogenic oscillations from the measured air flow.

13. The method as recited in claim 12, wherein said measuring step is performed during periods of apnea.

14. The system as recited in claim 12, wherein said measuring step is performed by a pneumotachograph having a tube that is capable of insertion into the mouth of a patient.

15. The system as recited in claim 12, wherein said measuring step is performed by a pneumotachograph having a tube that is capable of insertion into the tracheal cannula of a patient.

16. The method as recited in claim 12, further comprising the step of converting the cardiogenic oscillations to an electrical output signal.

17. The method as recited in claim 16, further comprising the step of converting said electrical output signal to a stream of digital data.

18. The method as recited in claim 17, further comprising the step of displaying said stream of digital data.

19. The method as recited in claim 12, further comprising the step of inferring cardiac output from said extracted cardiogenic oscillations.

20. The method as recited in claim 12, further comprising the step of continuously calculating cardiac output based upon said cardiogenic oscillations.

* * * * *